(12) United States Patent
Mailhe et al.

(10) Patent No.: US 9,907,666 B2
(45) Date of Patent: Mar. 6, 2018

(54) SCAPHOLUNATE STABILIZATION IMPLANT

(71) Applicants: BIOTECH ORTHO, Salon de Provence (FR); UNIVERSITE D'AIX MARSEILLE, Marseilles (FR)

(72) Inventors: Jean Mailhe, Pertuis (FR); Leatitia Rossi, La Fare les Oliviers (FR); Patrick Houvet, Boulogne Billancourt (FR); Frédéric Impellizzeri, Salon de Provence (FR)

(73) Assignee: Biotech Ortho and Universite D'aix Marseille, Salon de Provence and Marseilles (FR)

( * ) Notice: Subject to any disclaimer, the term of this patent is extended or adjusted under 35 U.S.C. 154(b) by 7 days.

(21) Appl. No.: 15/029,118

(22) PCT Filed: Oct. 15, 2014

(86) PCT No.: PCT/FR2014/052629
§ 371 (c)(1),
(2) Date: Apr. 13, 2016

(87) PCT Pub. No.: WO2015/059387
PCT Pub. Date: Apr. 30, 2015

(65) Prior Publication Data
US 2016/0250031 A1    Sep. 1, 2016

(30) Foreign Application Priority Data
Oct. 22, 2013   (FR) ...................... 13 60283

(51) Int. Cl.
*A61F 2/42* (2006.01)
*A61B 17/80* (2006.01)

(52) U.S. Cl.
CPC ........ *A61F 2/4261* (2013.01); *A61B 17/8061* (2013.01); *A61B 17/8085* (2013.01); *A61F 2002/4289* (2013.01); *A61F 2002/4292* (2013.01); *A61F 2250/0018* (2013.01); *A61F 2310/00023* (2013.01)

(58) Field of Classification Search
CPC ............ A61F 2/4261; A61F 2002/4287; A61F 2002/4289; A61F 2002/4292; A61B 17/80–17/8095
See application file for complete search history.

(56) References Cited

U.S. PATENT DOCUMENTS 5,690,631 A * 11/1997 Duncan .............. A61B 17/8085
606/281
2006/0235397 A1   10/2006 Sanders et al.
2011/0029023 A1   2/2011 Tornier

FOREIGN PATENT DOCUMENTS

FR           2951072 A1    4/2011

OTHER PUBLICATIONS

International Search Report for corresponding International Application No. PCT/FR2014/052629.

* cited by examiner

*Primary Examiner* — Thomas J Sweet
*Assistant Examiner* — Daniel Bissing
(74) *Attorney, Agent, or Firm* — Duane Morris LLP

(57) ABSTRACT

A scapholunate stabilisation implant includes a central part having an elastic deformation capacity enabling the traction movements of the implant, and two end parts having an elastic deformation capacity enabling the torsional movements of the implant, the end parts being provided with at least one hole through which the fixing screw is passed, the central part and the end parts being connected by rods that can withstand the torsional deformations of the implant.

19 Claims, 4 Drawing Sheets

SCAPHOLUNATE STABILIZATION IMPLANT

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention concerns a scapholunate stabilization implant.

2. Description of Related Art Including Information Disclosed Under 37 CFR 1.97 and 37 CFR 1.98

The scaphoid and the semilunate are two of the eight bones constituting the carpus of the hand. During a severe fall involving an impact on the wrist the intra-articular ligament connecting these two bones, called the scapholunate ligament, can suffer lesions such as a laceration, a tear . . . The failure of this ligament creates an instability which leads to an early arthrosis.

Interventions are available for the repair of this ligament depending on the extent of the injury:
  interventions on the soft tissues;
  fusions of bones.

If the lesion is taken care of early enough by a surgeon, the latter can perform a suture or a ligamentary reinsertion which is only feasible if the ligament is still vascularized. Ligamentary reinsertion associated to capsulodesis is the technique presently used most often. Whatever technique is used, if it allows bringing the bones closer together and to reduce the scaphoid in an efficient manner, after having suppressed intra-articular fibrosis, the result can be good. However, these techniques on soft tissues are to be reserved for dynamic instabilities or for static instabilities that are easily reducible. Although it is possible with these techniques to restore the dynamics of the wrist and although the danger of the appearance of arthrosis has been avoided, the injured ligament never regains its initial capacities.

In case the lesion is not quickly looked after, the damage caused by friction of the scaphoid and the semilunate maybe irreversible and bone fusion needs to be considered. Bone fusions radically modify the mechanics of the wrist. Although bone fusions are reliable over the long term, these interventions present numerous disadvantages, the main one being the risk of pseudarthrosis. Furthermore, these interventions are often stiffening in flexion and in extension so that the patient loses a good part of these capacities of movement. Lastly, the risk of a new rupture after anatomical repair of the ligament is not negligible.

In another extreme case, ablation of the two bones may have to be considered.

Also known are prosthetic devices as replacement of the scapholunate ligament.

Most often, these devices are constituted by two plates intended to be anchored in each of the two bones to be reconnected, or to be fastened on the latter, and by a rod or a wire for making the connection of said two plates.

The disadvantage of such devices is that they are generally constituted, in part, by metallic elements. So there is a risk of osseous adherence. In fact, when an implant is present in an organism over a lengthy period, the bone has a tendency to "re-grow" on the implant and to partially cover it. It can then be impossible to remove it in its entirety which can be problematic, particularly during subsequent surgical interventions.

Furthermore, presently available devices require, in most cases, immobilization of the wrist with a splint or a plaster cast for a duration of 6 to 8 weeks, which prevents any premature mobilization and leads to a stiffening of the wrist.

To remedy these disadvantages, a scapholunate stabilization implant has been proposed in document FR-2951072.

This stabilization implant of a generally trapezoid shape capable of replacing the broken scapholunate ligament or of reinforcing the injured scapholunate ligament, is constituted by a plate of oblong shape made of a material having a capacity of elastic deformation the ends of which being provided with at least one hole for the passage of fastening screws and the central part of which presents an opening delimited by two opposing sides, a spring of predetermined stiffness connecting two distant points, preferably two opposite points of said sides, this spring being positioned along the diagonal, in said opening.

This device makes possible in particular:
  supply of an implant which efficiently performs the functions of the scapholunate ligament,
  rapid and precise installation of this implant,
  feasibility of relative movements of the scaphoid and the semilunate, which is to say good functioning of the wrist.

Utilization of this device has nevertheless made it possible to observe that it was desirable to make a few significant modifications with the aim of improving its performance.

For example, according to the implant described in document FR-2951072, the geometry of the implant is such that it does not support well the twisting movements in a direction perpendicular to the plane of the implant whereas the scaphoid and the semilunate are two bones that turn, one in relation to the other during certain movements of the hand.

One aim of the present invention is to provide orthopedic surgeons with a simple stabilization implant that is flexible, resistant and not very invasive, creating a mechanical connection between the scaphoid and the semilunate, reproducing the role of the scapholunate ligament, allowing to reestablish the initial mobility of the wrist bones (scaphoid and semilunate) and without the disadvantages mentioned above.

The device has been designed for the purpose of enabling the relative movements of the scaphoid and the semilunate while resisting the stresses imposed on them.

BRIEF SUMMARY OF THE INVENTION

The scapholunate stabilization implant according to the invention includes a central part with a capacity of elastic deformation enabling the traction or compression movements of the implant, and two end parts with a capacity of elastic deformation enabling the twisting movements of the implant.

More precisely, the implant may feature a central part, a first end part and a second end part, the first and second end parts being each provided with at least one hole for the passage of fastening screws. The central part and the first and second end parts are connected respectively by a first and a second torsion bar capable of supporting twisting deformations of the implant.

In conformance with the invention, the central part may feature at least one central bar and lateral bars connected to the central bar by a plurality of parallel cross beams.

When a single central bar is used, it may be connected to one of the end parts and the lateral bars may be connected to the other end.

However, according to a preferred implementation of an implant according to the invention, the central part includes a first and a second central bar and lateral bars, each of the lateral bars being connected by a plurality of cross beams respectively to the first central bar and to the second central bar. The beams are preferably parallel to each other.

The device according to the invention offers several interesting advantages. In particular:
provide a solid implant which efficiently performs the functions of the scapholunate ligament,
permit a fast and precise installation of this implant,
enable relative movements of the scaphoid and the semilunate, which is to say a physiological functioning of the wrist,
decouple the mechanisms of pulling and twisting sustained by the ligament.

According to an advantageous implementation, the beams present each a first end connected to one of the first and second central bars, a second end connected to one of the first and second lateral bars and a central portion, the beams having a decreasing section of their first and their second end, in the direction of their central portion.

According to a particular possibility of implementation of the implant, the central part of the implant may present, in its middle, a transversal spacing which separates the first and second central bars and is delimited by the lateral bars of the central part. The transversal spacing, which is greater than the spacing between the beams, allows for greater compression or extension of the implant.

According to another example of implementation, the lateral ends may present a general triangular shape and each end of the scapholunate stabilization implant is provided with two through-holes for screws.

According to one example of implementation, the lateral ends have the shape of an asymmetric arrow, the fins of which feature the through-holes for the fastening screws, and the central bars of which allow to connect said ends to the central part of the implant, constitute the torsion bars of said implant.

According to another aspect of the invention, the implant may feature, on at least one of its end parts, a positioning lug, or two diametrically opposed positioning lugs, said lug(s) being provided with a hole for the passage of a temporary stabilization pin, this (these) positioning lug(s) being placed in proximity of the through-holes for the fastening screws.

According to an advantageous example of implementation, the positioning lugs are divisible, so that when the implant has been fastened on the patient's bones by means of the fastening screws, these positioning lugs, now no longer useful, can be removed.

According to a preferred implementation, the scapholunate stabilization implant may be made of any biocompatible material presenting the necessary robustness and elasticity.

According to an advantageous implementation, the lateral ends of the implant are made of polymer, such as Polyetheretherketone (PEEK) and the central part is made of a titanium alloy, the bars connecting the central part to the lateral ends being made of titanium alloy encapsulated in PEEK.

BRIEF DESCRIPTION OF THE DRAWINGS

The afore-mentioned aims, characteristics and advantages and still more will become clearer from the detailed description below and the attached drawings in which.

Figure 1:
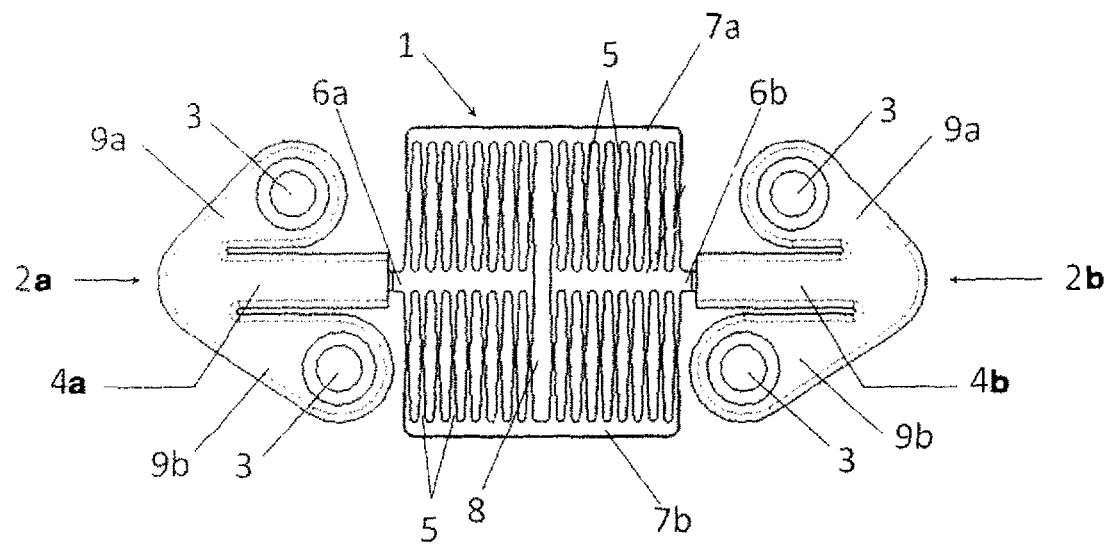
FIG. 1 is a top view of a first example of implementation of the scapholunate stabilization implant, shown in a position at rest.

Reference is made to these drawings to describe interesting, although by no means limiting examples of implementation of the scapholunate stabilization implant, according to the invention.

DETAILED DESCRIPTION OF THE INVENTION

This essentially symmetric scapholunate stabilization implant is constituted by a central part 1 with a capacity of elastic deformation enabling the pulling movements of the implant, and by two end parts 2a, 2b with a capacity of elastic deformation enabling the twisting movements of the implant, these end parts being provided with at least one hole 3 for the passage of fastening screws, said central part 1 and said end parts 2a, 2b being connected through the intermediary of torsion bars 4a, 4b fit for supporting the twisting deformations of the implant.

According to the example shown, each end part 2a, 2b of the stabilization implant is provided with two spaced through-holes 3 for fastening screws. These fastening screws (not shown) are, for example, of the double threaded, self-cutting type and therefore capable of automatically cutting, as they are being screwed in, the tapping of the holes 3 which are advantageously of conical shape.

The four holes 3 which the stabilization implant is provided with form the general shape of a trapeze, this general shape being dictated by the anatomy of the bones to be connected.

The scapholunate stabilization implant presents a general shape of an elongated hexagon.

The central part 1 of the implant presents a rectangular or approximately rectangular shape. This central part includes central bars 6a and 6b and lateral bars 7a, 7b connected by a plurality of parallel cross beams 5.

Figure 2:
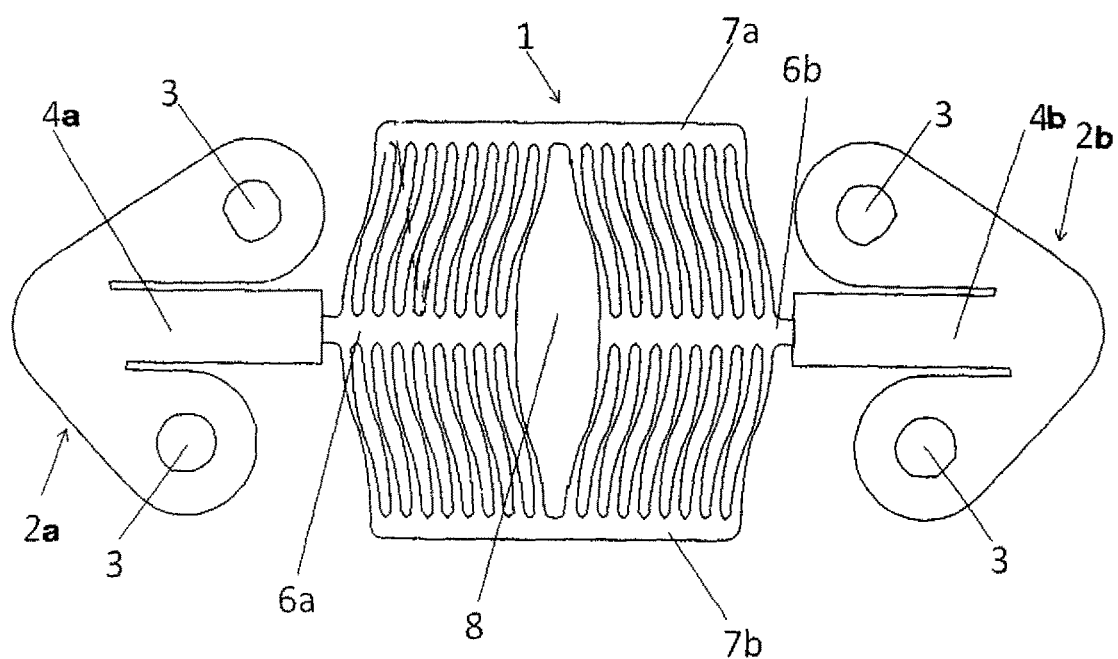
FIG. 2 is an analog view to FIG. 1, showing the implant according to the invention subjected to a tension load.

Advantageously, the beams 5 present a decreasing section in the direction of their central portion. This characteristic gives the central part an elasticity providing it in this manner with better tolerance of deformation by elongation, under the effect of a tension force for example (see FIG. 2). In the symmetric construction shown a same number of beams 5 connects respectively each central bar 6a, 6b to the lateral bars 7a, 7b.

Figure 3:
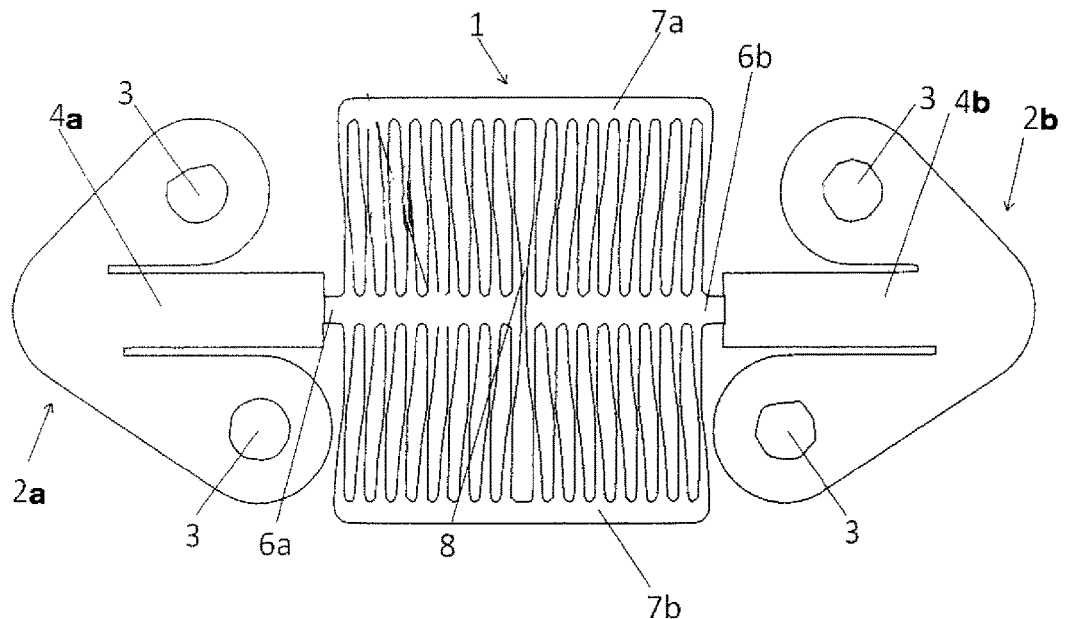
FIG. 3 is an analog view to FIG. 1, showing the implant according to the invention subjected to a compression load.
Figure 4:
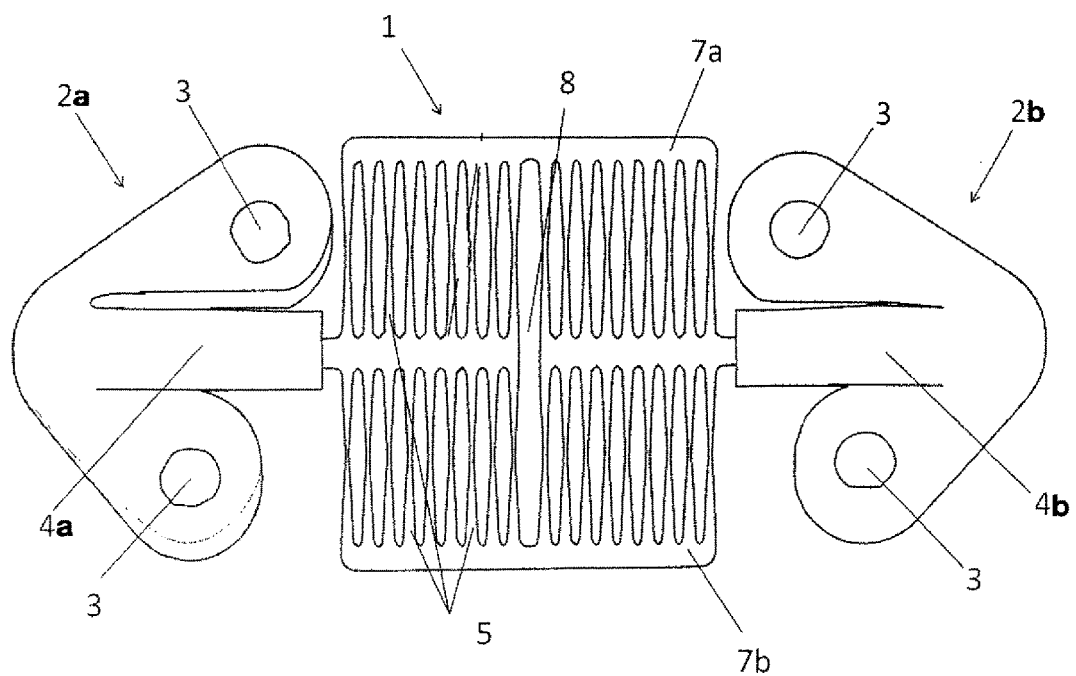
FIG. 4 is an analog view to FIG. 1, showing the implant according to the invention subjected to a twisting strain.
Figure 5:
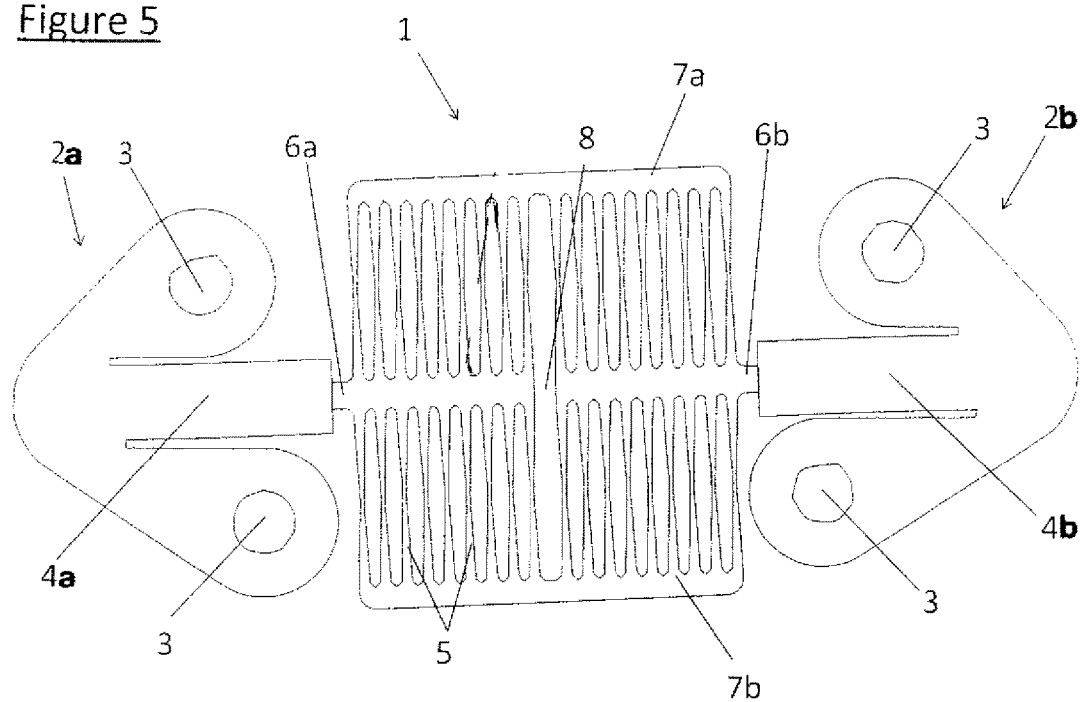
FIG. 5 is an analog view to FIG. 1, showing the implant according to the invention subjected to a bending stress of the implant.

Preferably, the central part 1 presents, in its middle, a transversal space 8 delimited by the lateral bars 7a, 7b. This space enables the central part to support the compression movements to which the implant may be subjected (see FIG. 3).

The central part 1 formed in this manner has the purpose of maximizing the capacity of the implant to support deformation. It allows elongation in traction as well as a transmission of load.

The end parts 2a, 2b present a general triangular shape. This shape allows in particular to increase the useful length of the implant.

More precisely, these ends 2 have the shape of an asymmetric arrow, the fins 9a, 9b of which feature the through-holes 3 for fastening screws and their central bars which make it possible to connect said ends 2a, 2b to the central part 1 of the implant constitute the torsion bars 4a, 4b of said implant.

These torsion bars enable the implant to support the twisting strain the latter is subjected to and, consequently, they facilitate the twisting movement the ligament is subjected to.

In one implementation where the implant according to the invention is executed in several parts, the ends of the central bars 6a, 6b are extended so that they can be implanted in the bars of the end parts 2a, 2b, for example by encapsulating the latter on said ends of the central bars 6a, 6b respectively turned towards the end parts 2a, 2b.

Figure 6:
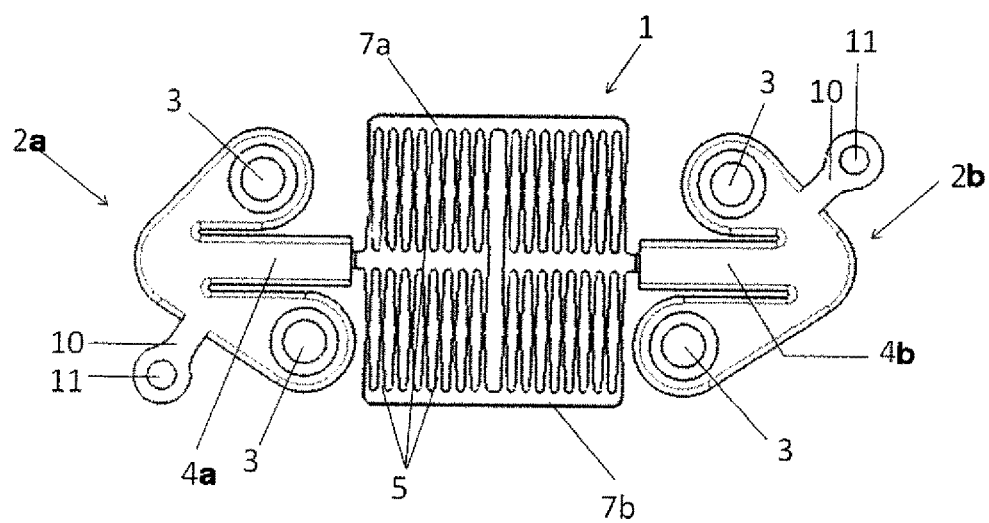
FIG. 6 is an analog view to FIG. 1 and showing another example of implementation of the scapholunate stabilization implant according to the invention.
Figure 7:
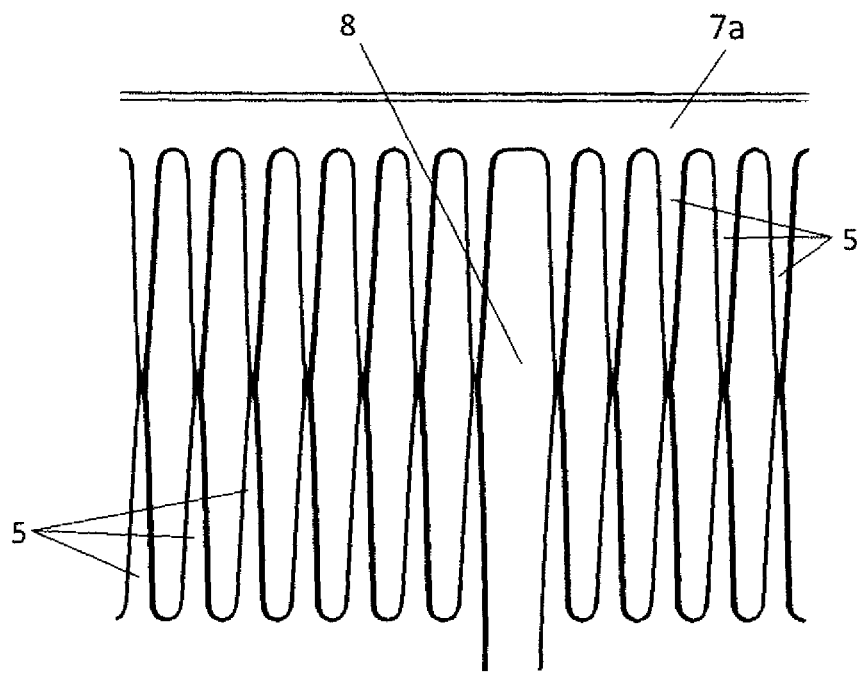
FIG. 7 is a detail view of the central part of the implant.
Figure 8:
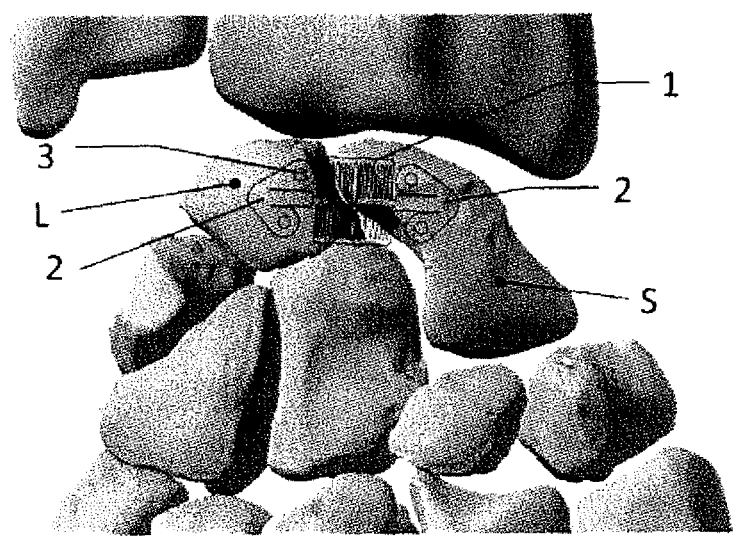
FIG. 8 is a view showing the implant positioned on the scaphoid and the semilunate of a hand.

The implant according to the invention is also remarkable in that it is provided with at least one positioning lug 10 featuring a hole 11 for the passage of a temporary stabilization pin. According to the example of implementation shown in FIG. 6, the implant features two lugs 10 diametrically opposed and placed in proximity of the through-holes 3 for the fastening screws, each of the lugs 10 being provided with a hole 11.

In effect, before fastening the scapholunate implant using the fastening screws in each of the bones concerned (scaphoid S and semilunate L), the surgeon is first induced to stabilize the implant relative to these bones, then to perform drills in said bones for the placement of said screws.

Advantageously, the positioning lugs 10 are divisible so that when the implant has been fastened on the patient's bones by means of the fastening screws, these positioning lugs, now no longer useful, can be removed.

The scapholunate stabilization implant is made of any biocompatible material presenting the necessary robustness and elasticity.

Advantageously, the central part 1 of the implant is made of a titanium alloy, and the end parts 2 of said implant are made of polymer, such as Polyetheretherketone (PEEK), the torsion bars 4a, 4b connecting the central part 1 to the end parts 2a, 2b being made of titanium alloy encapsulated in PEEK.

PEEK possesses mechanical characteristics that are very interesting because they allow extensive deformation while ensuring a return to its shape in the position of equilibrium. This material is also advantageous to the extent that it is radiolucent, and that it does not sustain osseous adherence, which means that it can easily be removed even after having remained in place in the organism for several years.

The titanium alloy (such as, for example, TA6V Eli or Nitinol®) constituting the central part whose particular geometry of the beams it is composed of gives it a general shape of combs facing each other in pairs, allows enhancing its sturdiness.

The length of the implant must be sufficient to allow fastening one of its ends on the scaphoid S, and fastening its other end on the semilunate L. It may for example measure in the order of 20 mm of length, and in the order of 8 mm of width.

The invention claimed is:

1. A scapholunate stabilization implant, including a central part, a first end part and a second end part, the first and second end parts being provided each with at least one through-hole for the passage of fastening screws, in which the central part and said first and second end parts are connected respectively by a first and a second torsion bar and in which the central part of the implant includes a first and a second central bar and lateral bars each of the lateral bars being connected, by a plurality of cross beams, respectively to the first and the second central bar and wherein the central part presents, in its middle, a transversal spacing separating the first and second central bars and delimited by the lateral bars.

2. The scapholunate stabilization implant according to claim 1, characterized in that the beams each present a first end connected to one of the first and second central bars, a second end connected to one of the first and second lateral bars and a central portion, the beams having a decreasing section of their first and second end, in the direction of their central portion.

3. The scapholunate stabilization implant according to claim 1, characterized in that the end parts present a shape having three non-aligned vertices and each end part of the scapholunate stabilization implant is provided with two through-holes for screws.

4. The scapholunate stabilization implant according to claim 1, characterized in that the end parts have the shape of an asymmetric arrow having fins, and wherein the fins feature the through-holes for fastening screws, and their central rods which enable said ends to be connected to the central part of the implant constitute the torsion bars of said implant.

5. The scapholunate stabilization implant according to claim 1, characterized in that the implant features, on at least one of its end parts a positioning lug or two diametrically opposed positioning lugs, said lug(s) being provided with a hole for the passage of a temporary stabilization pin, this or these positioning lug(s) being placed in proximity of the through-holes for the fastening screws.

6. The scapholunate stabilization implant according to claim 5, characterized in that the positioning lugs are divisible so that when the implant has been fastened on the patient's bones by means of the fastening screws, these positioning lugs, now no longer useful, can be removed.

7. The scapholunate stabilization implant according to claim 1, characterized in that it is made of a biocompatible material presenting the necessary robustness and elasticity.

8. The scapholunate stabilization implant according to claim 1, characterized in that the central part of the implant is made of a titanium alloy, and the end parts of said implant are made of a polymer, the torsion bars connecting the central part to the end parts being thus executed in a titanium alloy encapsulated in polymer.

9. The scapholunate stabilization implant according to claim 8, wherein the polymer is Polyetheretherketone (PEEK).

10. A scapholunate stabilization implant, including a central part, a first end part and a second end part, the first and second end parts being provided each with at least one through-hole for the passage of fastening screws, in which the central part and said first and second end parts are connected respectively by a first and a second torsion bar and in which the central part of the implant includes a first and a second central bar and lateral bars each of the lateral bars being connected, by a plurality of cross beams, respectively to the first and the second central bar, and wherein the end parts have the shape of an asymmetric arrow having fins, and wherein the fins feature the through-holes for fastening screws, and their central rods which enable said ends to be connected to the central part of the implant constitute the torsion bars of said implant.

11. The scapholunate stabilization implant according to claim 10, characterized in that the beams each present a first end connected to one of the first and second central bars, a second end connected to one of the first and second lateral bars and a central portion, the beams having a decreasing section of their first and second end, in the direction of their central portion.

12. The scapholunate stabilization implant according to claim 10, characterized in that the end parts present a shape having three non-aligned vertices and each end part of the scapholunate stabilization implant is provided with two through-holes for screws.

13. The scapholunate stabilization implant according to claim 10, characterized in that the implant features, on at least one of its end parts a positioning lug or two diametrically opposed positioning lugs, said lug(s) being provided with a hole for the passage of a temporary stabilization pin, this or these positioning lug(s) being placed in proximity of the through-holes for the fastening screws.

14. The scapholunate stabilization implant according to claim 13, characterized in that the positioning lugs are divisible so that when the implant has been fastened on the patient's bones by means of the fastening screws, these positioning lugs, now no longer useful, can be removed.

15. A scapholunate stabilization implant, including a central part, a first end part and a second end part, the first and second end parts being provided each with at least one through-hole for the passage of fastening screws, in which the central part and said first and second end parts are connected respectively by a first and a second torsion bar and in which the central part of the implant includes a first and a second central bar and lateral bars each of the lateral bars being connected, by a plurality of cross beams, respectively to the first and the second central bar, wherein the central part of the implant is made of a titanium alloy, and the end parts of said implant are made of a polymer, the torsion bars connecting the central part to the end parts being thus executed in a titanium alloy encapsulated in polymer.

16. The scapholunate stabilization implant according to claim 15, characterized in that the beams each present a first end connected to one of the first and second central bars, a second end connected to one of the first and second lateral bars and a central portion, the beams having a decreasing section of their first and second end, in the direction of their central portion.

17. The scapholunate stabilization implant according to claim 15, characterized in that the end parts present a shape having three non-aligned vertices and each end part of the scapholunate stabilization implant is provided with two through-holes for screws.

18. The scapholunate stabilization implant according to claim 15, characterized in that the implant features, on at least one of its end parts a positioning lug or two diametrically opposed positioning lugs, said lug(s) being provided with a hole for the passage of a temporary stabilization pin, this or these positioning lug(s) being placed in proximity of the through-holes for the fastening screws.

19. The scapholunate stabilization implant according to claim 18, characterized in that the positioning lugs are divisible so that when the implant has been fastened on the patient's bones by means of the fastening screws, these positioning lugs, now no longer useful, can be removed.

* * * * *